United States Patent [19]
Hagen

[11] Patent Number: 5,330,470
[45] Date of Patent: Jul. 19, 1994

[54] ELECTRO-SURGICAL TREATMENT INSTRUMENT

[75] Inventor: Alfred Hagen, Tuttlingen, Fed. Rep. of Germany

[73] Assignee: Delma elektro-und medizinische Apparatebau Gesellschaft mbH, Tuttlingen, Fed. Rep. of Germany

[21] Appl. No.: 907,936

[22] Filed: Jul. 2, 1992

[30] Foreign Application Priority Data

Jul. 4, 1991 [DE] Fed. Rep. of Germany ....... 4122219

[51] Int. Cl.⁵ .............................................. A61B 17/39
[52] U.S. Cl. ...................................... 606/42; 606/48; 606/50
[58] Field of Search .............................. 606/48, 50, 42

[56] References Cited

U.S. PATENT DOCUMENTS

| 4,034,762 | 7/1977 | Cosens et al. | 606/50 X |
| 4,483,338 | 11/1984 | Bloom | |
| 4,706,667 | 11/1987 | Roos | 606/48 |
| 5,007,908 | 4/1991 | Rydell | 606/50 X |

FOREIGN PATENT DOCUMENTS

| 256415 | 5/1988 | Fed. Rep. of Germany | 606/48 |
| 3510586 C2 | 7/2988 | Fed. Rep. of Germany | |
| 2165761A | 9/1985 | United Kingdom | |
| 8503859 | 9/1985 | World Int. Prop. O. | 606/50 |

Primary Examiner—Lee S. Cohen
Attorney, Agent, or Firm—Townsend and Townsend Khourie and Crew

[57] ABSTRACT

The invention relates to an electro-surgical treatment instrument with a holder 16 connectable to a radio frequency generator with two electrodes 11, 12 being arranged at the proximal end of the holder which can be brought into contact with the tissue of a patient, which are mutually insulated relative to one another and which are fed with rf-voltage. A cutting electrode 13 is centrally provided.

15 Claims, 2 Drawing Sheets

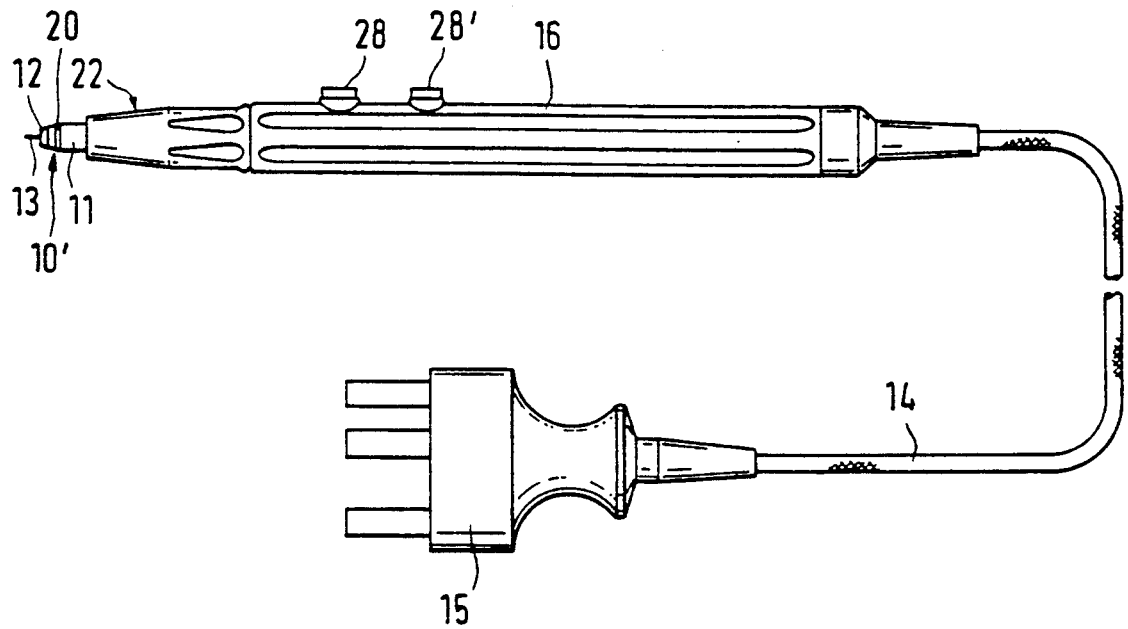
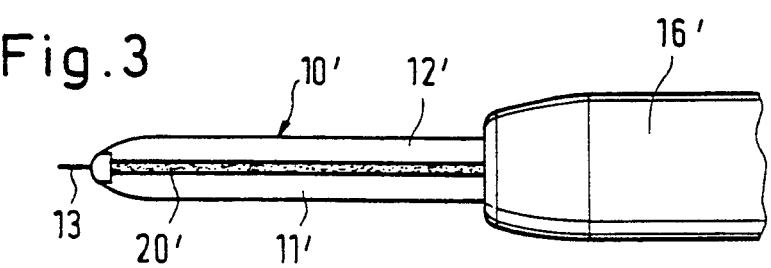
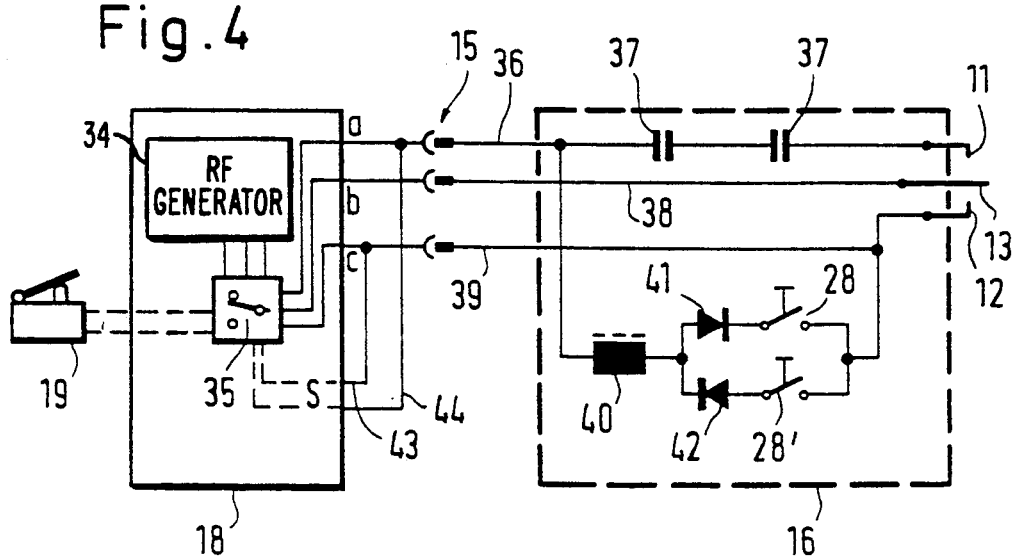

ELECTRO-SURGICAL TREATMENT INSTRUMENT

BACKGROUND OF THE INVENTION

The invention relates to an electro-surgical treatment instrument comprising a holder connectable to a high frequency generator with at least two electrodes provided at the proximal end of the holder which can be brought into contact with the tissue of a patient.

In a known treatment instrument of this kind, (DE 34 23 352 C2) the two electrodes are arranged alongside one another with respect to the axis of the treatment instrument and formed as the branches of a pair of tweezers. In this way, tissue regions of a patient which can be grasped in a tweezer-like manner with the electrodes can be subjected to bi-polar coagulation.

If, however, tissue regions are to be coagulated which cannot simply be grasped in a simple tweezer-like manner, then coagulation requires very much attention and skill on behalf of the operator. This is because he must then select the electrode spacing necessary for bi-polar coagulation by pressing the tweezer-like electrodes together and adapt it as necessary to the resulting coagulation.

SUMMARY OF THE INVENTION

The object of the present invention is to provide electro-surgical treatment instrument that can carry out bi-polar coagulation in trouble-free manner without having to set the electrode spacing during a surgical operation and without the danger existing that the tissue becomes caught up on the electrodes.

This object is satisfied by an electro-surgical treatment instrument as initially defined, but characterised in that the two electrodes are formed at least partly at the side surfaces of an elongate body; and in that their spacing, which is determined by an insulating separating layer, is so small that a coagulation current flows at least on one sided contact of the body against the tissue.

The elongate body preferably has only rounded surfaces and no edges or corners; in particular it has a circular cross-section and is tapered and/or rounded at the front end.

The fact that the jacket or peripheral surface of the coagulation body is smooth, i.e. extensively free of projections, and rounded makes trouble-free sliding on the surface on the tissue possible. Thus, injuries through displacement of the body along the tissue are avoided in just the same way as the coagulation body becoming caught up on the tissue.

Another advantage of the treatment instrument of the invention is that the spacing in between the coagulation electrodes that is required for coagulation is precisely determined. The operator can thus fully concentrate on the necessary operation during the treatment. In particular, he only needs to travel along the tissue to be coagulated with the fixedly spaced electrodes without having to pay attention to the maintenance of a suitable electrode spacing.

Moreover, the lateral position of the coagulation region allows the treatment instrument handled and guided comfortably.

A first advantageous embodiment, the two electrodes are annular and are arranged behind one another. The front electrode may be a spherical, parabolic conical metallic block or ring and the rear electrode may be a cylindrical metal sleeve, the electrodes being preferably concentric to one another. An insulating ring, concentric to the electrodes, is provided between the electrodes.

In a specific embodiment, the insulating ring, which is rearwardly directed, extends within the rear electrode, which is formed as a sleeve, preferably in a fitted seat. A metal tube, extending rearwardly from the front electrode, is arranged within the insulating ring, again preferably in a fitted seat.

In these above embodiments, the coagulation region is thus symmetrically arranged around the cylindrical coagulation body.

The arrangement of the coagulation electrodes can, however, also be effected so that the electrodes are formed by two half shells or half cylinders which are mutually separated by an axial separating layer. This embodiment provides axially extending coagulation regions on two diametrically opposed sides of the coagulation body.

The coagulation instrument as described above can be used together with a central cutting electrode arranged in insulated manner within the two coagulation electrodes. The cutting electrode can project forwardly out of the coagulation body by a defined amount and is preferably formed as a needle-like wire.

The degree of projection of the cutting electrode in front of the coagulation body should advantageously be adjustable. For this purpose, the cutting electrode is preferably formed as an axial thin metal pin or metal wire extending within at least one annular electrode, the annular electrode being axially displaceable relative to the cutting electrode which is axially fixedly arranged on the holder.

In a first advantageous, development of this embodiment the electrodes and the insulating layers form a constructional unit together with the mounting elements, in particular a constructional unit which is formed as a cap which is arranged on the proximal end of the holder. Moreover, the cap is advantageously axially adjustable relative to the holder and is in particular screwable relative thereto.

Since a cutting electrode can wear in the course of time, and can also be damaged in use, it should preferably be removable, i.e. also interchangeable. For this purpose, the cutting electrode is removably arranged from the instrument.

In one advantageous realisation of this instrument, the front annular electrode is the reference electrode. Moreover, the cutting electrode may be axially guided through the other two electrodes, which are of hollow construction, and through the insulation which is located between them. The cutting electrode is preferably mounted via a plug connector to an axial feedline fixedly arranged in the holder. An insulating tube through which the cutting electrode axially passes is expediently inserted into the front electrode.

An advantageous combination of two coagulation electrodes and a fixedly arranged cutting electrode is achieved when two axially displaced hollow coagulation electrodes are arranged concentric to one another and when a forwardly projecting cutting electrode is arranged within these coagulation electrodes.

From the control viewpoint, the invention preferably provides an electro-surgical treatment instrument comprising a holder connectable to an rf generator with a coagulation electrode pair and a cutting electrode pair being provided at the proximal end of the holder. The instrument can be selectively energised from the rf-generator with a suitable rf-voltage or a suitable rf-current respectively and at least one of the high frequency feedline pairs is additionally energised by a low frequency control current which is kept away from the active electrode by a high pass filter pass and is passed to a control circuit arrangement provided at the holder. The control circuit arrangement is separated from the radio frequency by a low pass filter from the ratio frequency and delivers a switching signal to a change-over device connected to the rf-generator on switching the control current in the one or other direction. The change-over device applies a suitable radio frequency current to the coagulation electrode pair or to the cutting electrode pair depending on the direction of the control current.

The control current is an alternating current and the control circuit arrangement has two switches connected in parallel and respectively lying in series with an oppositely poled rectifier. A switching arrangement is provided in the change-over device which, depending on which of the two control switches is closed, energises either the coagulation electrode pair or the cutting electrode pair with the radio frequency current provided therefor.

Through the superimposition of the radio frequency current and a low frequency control current the same lines that are used for the supply of the radio frequency current can also be used to conduct the control current.

The front one of the two coagulation electrodes is preferably the reference electrode which is also active during the cutting.

The invention will be described in more detail in the following by way of example and with reference to the drawings in which are shown:

BRIEF DESCRIPTION OF THE DRAWINGS

FIG. 1 a plan view of an electro-surgical radio frequency treatment instrument with connection cable and plug, FIG. 2 a part longitudinal section through the front part of the treatment instrument of FIG. 1 which contains the various electrodes, FIG. 3 a side view of the front part of a further embodiment of the treatment instrument, and FIG. 4 a schematic, greatly simplified circuit diagram of the radio frequency electronic switching circuit and also the radio frequency and control current lines to the electrodes of the treatment instrument in accordance with FIGS. 1 to 3.

DESCRIPTION OF THE PREFERRED EMBODIMENT

Figure 2:
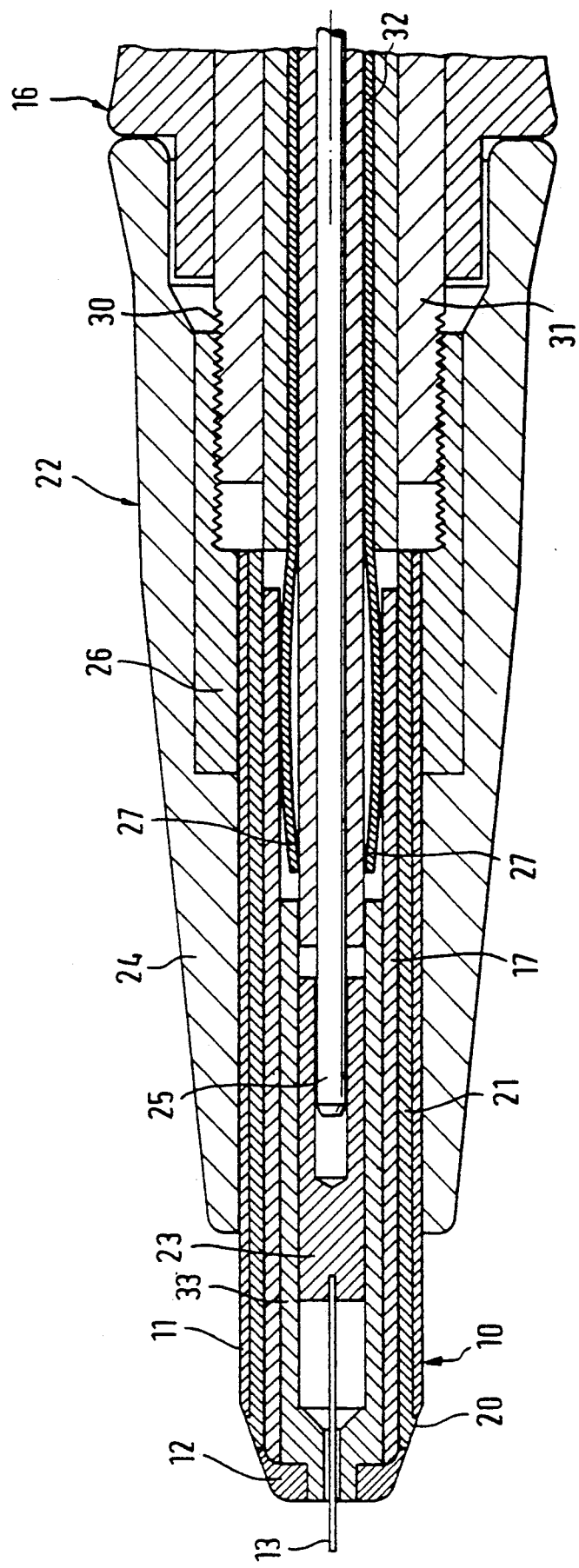

In FIGS. 1-3 components which correspond to one another are designated by the same reference numerals.

The electro-surgical treatment instrument illustrated in FIG. 1 has a holder 16. A cap 22 is arranged by means of a thread, a bayonet connection or a slider arrangement at the proximal end of the holder, i.e. at its left-hand end in FIG. 1. An electrode arrangement projects forwardly out of the cap and comprises a cylindrical rear coagulation electrode 11, an annular front reference electrode 12, and a cutting electrode 13 which projects forwardly from the reference electrode 12.

A cable 14 is connected to the distal end of the holder 16 and is provided at its other end with a plug 15 for connection to a radio frequency electronic circuit 18 (FIG. 4). The releasability of the cable 14 from the radio frequency electronic switching circuit 18 is necessary because such instruments must be removed from the electronics for sterilisation. For the same reason, the cable 14 is also connected to the distal end of the holder 16 by a plug connection.

Two touch switches 28, 28' are provided, one behind the other, on the holder 16 for selectively switching cutting or coagulation operations on the instrument. A slider switch however could also be used. Furthermore, the actuation can take place via a foot switch 19 (FIG. 4) which is directly connected to the radio frequency electronic circuit 18.

In accordance with FIG. 2, the cap 22 a slightly conical hollow body that has an insulating grip sleeve 24 into which an internally threaded metal sleeve 26 is fixedly inserted. The coagulation electrode 11 is coaxially mounted within the internally threaded sleeve 26 and projects at its proximal end out of the grip sleeve 24. An insulating tube 21 with a front insulating ring 20 is coaxially mounted within the coagulation electrode 11. Insulating ring 20 contacts the front end surface of the coagulation electrode 11 and the rear end surface of a reference electrode 12 arranged in front of the coagulation electrode 11. The reference electrode 12 is formed as a metal ring with a forwardly tapered and rounded peripheral surface. The peripheral surfaces of the reference electrode 12, of the insulating ring 20 and of the coagulation electrode 11 merge continuously into one another to form the smooth outer surface of the front end of the instrument.

The reference electrode 12 is connected as its rear side with a metal tube 17 which is coaxially mounted within the insulating tube 21 and forms at its rear end a sleeve for receiving a resilient plug contact 27 secured to the holder 16.

A second insulating tube 33 is arranged within the metal tube 17 and houses the cutting electrode 13 and its connection sleeve 23, which is arranged at the rear end of the cutting electrode. A metal tube 31 provided with an external thread 30 projects from the front end of the holder 16. Threaded sleeve 26 of cap 22 matts with external thread 30. The insulated feedlines 25 and 32 for the cutting electrode 13 are separated by a third insulating tube 45 and for the reference electrode 12 are also arranged within the metal tube 31 which also serves as an insulated electrical feedline to the coagulation electrode 11.

The feedline 25 for the cutting electrode 13 is formed at its front end as a plug which is releasably inserted into the sleeve 23 of the cutting electrode 13.

In order to assemble the treatment instruments for operation the cutting electrode 13 of the sleeve 23 is first placed on to the plug at the front end of the feedline 25. The screw cap 22 is subsequently pushed onto the front end of the holder 16 so that the cutting electrode 13 enters into the insulating tube 33 and the plug contact 27 enters into the metal tube 17. Also, the inner threaded sleeve 26 of the threaded cap 22 enters into threaded engagement with the outer threaded sleeve 31 of the holder 16 and can thus be screwed onto the holder 16.

As the cap 22 is screwed into place, the cutting electrode 13 projects further out of the central opening of the reference electrode 12 forwardly through the insulating tube 33 which is arranged in the interior of the metal tube 17 and tapers within the central opening of the electrode 12. Through screwing the screw cap 22 on by differing amounts, one can thus ensure that the cutting electrode 13 projects to a greater or lesser degree out of the front end of the coagulation body 10.

In accordance with FIG. 3, two metallic half shells which are mutually insulated by separating layer 20' can also emerge from the holder 16' and form, together with the separating layer 20', the coagulation body 10' consisting of the coagulation electrode 11' and the reference electrode 12'. A forwardly projecting cutting electrode 13 is centrally arranged and insulated from the reference electrode 12' and coagulation electrode 11'.

As FIG. 4 schematically shows, the supply of electrodes 11, 12, 13 with rf-voltage or rf-current takes place from an rf-generator 34 which is a component of the radio frequency electronic circuit 18. The rf-generator 34 can deliver both a radio frequency current which is suitable for cutting and also a radio frequency current which is suitable for coagulation, this is determined by a switch-over device 35. A switch-over device 35 applies the suitable rf-voltage via outputs a, b, and c and the plug 15 either to the coagulation electrode pair 11, 12 or to the cutting electrode pair 12, 13.

In the feedline 36 which leads to the coagulation electrode 11 there are arranged, within the holder 16, one or two capacitors 37 which serve as a high-pass filter. The rf-outputs b, c are in contrast connected by feedlines 38, 39 directly to the cutting electrode 13 or to the reference electrode 12. A choke 40, which serves as a low-pass filter for a low frequency control current, branches off from the feedline 36 before the capacitors 37 and is connected via two diodes 41, 42. The diodes 41, 42 serve as rectifiers and which are connected parallel to one another, and via touch switches 28, 28' which are connected after the diodes 41, 42 to the feedline 39 for the reference electrode 12 which is grounded. Moreover, two lines 43, 44 of an AC control voltage output S of the radio frequency electronic switching circuit 18 are connected to the rf outputs a, c.

If, the operator actuates the touch switch 28 for cutting operation, then the voltage of the control output S is short-circuited and a low frequency current flows in one direction via the choke 40 and the diode 41 into the switching device 35, switching device 35 then applies the rf-voltage required for cutting operation to the rf-outputs b, c which are connected to the cutting electrode 13 and to the reference electrode 12, respectively.

If, on the other hand, the touch switch 28' for coagulation operation is closed, then a corresponding low frequency control current flows in the opposite direction via the choke 40 and the diode 42, whereupon the switching device 35 applies an rf-voltage suitable for bi-polar coagulation to the outputs a, c so that the coagulation electrode 11 and the reference electrode 12, which now also serves as a coagulation electrode, are supplied with the rf-voltage required for the coagulation or with the rf-current required for the coagulation.

During a surgical operation, the operator thus only needs to press one or other of the touch switches 28 in order to selectively cut or coagulate with the treatment instrument.

I claim:

1. An electro-surgical treatment instrument for cutting and coagulating a tissue with a high frequency current comprising:
    a holder having a proximal end for placement near the tissue and a distal end;
    first and second coagulation electrodes movably coupled to the proximal end of the holder so that the coagulation electrodes can be brought into contact with the tissue during an operation;
    a cutting electrode fixed to the holder and extending from the proximal end, the coagulation electrodes being axially displaceable relative to the cutting electrode and the holder;
    a radio frequency generator connected to the distal end of the holder, the generator supplying the high frequency current to the first and second coagulation electrodes and the cutting electrode; and
    an annular insulation layer disposed between the first and second coagulation electrodes, the insulation layer providing a spacing between said coagulation electrodes which is small enough so that the high frequency current flows between said coagulation electrodes to coagulate the tissue when the instrument is brought into contact with the tissue.

2. The device of claim 1 wherein the holder is essentially cylindrical and tapered forwardly at the proximal end.

3. The device of claim 1 wherein the holder has a smooth exterior surface.

4. The device of claim 1 wherein the first coagulation electrode is positioned closer to the proximal end of the holder than the second coagulation electrode.

5. The device of claim 1 wherein the first and second coagulation electrodes are concentric to each other, the first coagulation electrode having a conical shape and the second coagulation electrode having an annular shape so that the second coagulation electrode forms a sleeve around the proximal end of the holder.

6. The device of claim 1 wherein the insulation layer is concentric to the first and second coagulation electrodes.

7. The device of claim 1 further comprising a metal tube extending from the first coagulation electrode towards the distal end of the holder, the metal tube connecting the first coagulation electrode with the radio frequency generator, and a tubular projection extending from the insulation layer towards the distal end of the holder, the tubular projection forming a concentric sleeve around the metal tube which insulates the metal tube from the second coagulation electrode.

8. The device of claim 1 wherein the first and second coagulation electrodes each form a half cylinder on either side of the holder and an axial separating layer is disposed along the center of the holder to separate the first and second coagulation electrodes.

9. The device according to claim 1 further comprising a cap threadably mounted to the holder, the cap forming an exterior sleeve around the proximal end of the holder, the first and second coagulation electrodes and the insulation layer being fixed to the cap.

10. The device according to claim 9 wherein the cap is rotatable with respect to the holder so that the cap, the first and second coagulation electrodes and the insulation layer move axially with respect to the holder and the cutting electrode when the cap is rotated with respect to the holder.

11. The device according to claim 1 wherein the first coagulation electrode is a reference electrode for the second coagulation electrode and the cutting electrode.

12. The device according to claim 1 wherein the cutting electrode is axially guidable through the first and second coagulation electrodes and the annular insulation layer.

13. The device according to claim 1 further comprising an insulating tube disposed between the cutting electrode and the first and second coagulation electrodes.

14. The device according to claim 1 further comprising means for controlling the radio frequency generator so to selectively apply the high frequency current to one of the second coagulation electrode and the cutting electrode, the cutting electrode and the first coagulation electrode being operable for cutting the tissue when the high frequency current is applied to the cutting electrode and the first and second coagulation electrodes being operable for coagulating the tissue when the high frequency current is applied to the second coagulation electrode.

15. An electro-surgical treatment instrument for cutting and coagulating a tissue with a high frequency current comprising:

a holder having a proximal end for placement near the tissue and a distal end;

first and second coagulation electrodes movably coupled to the proximal end of the holder so that the electrodes can be brought into contact with the tissue during an operation;

a small area cutting electrode removably mounted to the proximal end of the holder with at least one of the coagulation electrodes and being fixed to the holder, the coagulation electrodes being axially displaceable relative to the cutting electrode;

a radio frequency generator connected to the distal end of the holder, the generator supplying the high frequency current to the first and second coagulation electrodes and the cutting electrode; and an annular insulation layer disposed between the first and second coagulation electrodes, the insulation layer providing a spacing between said coagulation electrodes, the spacing being small enough so that the high frequency current flows between said coagulation electrodes to coagulate the tissue when the instrument is brought into contact with the tissue.

\* \* \* \* \*